United States Patent
Harpas et al.

(10) Patent No.: US 8,679,025 B2
(45) Date of Patent: Mar. 25, 2014

(54) METHOD FOR DETERMINATION OF CARDIAC OUTPUT

(75) Inventors: Peter Chris Harpas, New South Wales (AU); Ahmad M. Qasem, New South Wales (AU)

(73) Assignee: AtCor Medical Pty Ltd, West Ryde, NSW (AU)

( * ) Notice: Subject to any disclaimer, the term of this patent is extended or adjusted under 35 U.S.C. 154(b) by 1252 days.

(21) Appl. No.: 12/438,895

(22) PCT Filed: Aug. 3, 2007

(86) PCT No.: PCT/AU2007/001090
§ 371 (c)(1),
(2), (4) Date: Aug. 20, 2009

(87) PCT Pub. No.: WO2008/025053
PCT Pub. Date: Mar. 6, 2008

(65) Prior Publication Data
US 2010/0016735 A1   Jan. 21, 2010

(30) Foreign Application Priority Data
Aug. 31, 2006   (AU) .................................. 2006904754

(51) Int. Cl.
*A61B 5/02* (2006.01)
(52) U.S. Cl.
USPC .......................................................... 600/485
(58) Field of Classification Search
USPC ...................... 600/481–488, 500–508, 529
See application file for complete search history.

(56) References Cited

U.S. PATENT DOCUMENTS

| | | | | |
|---|---|---|---|---|
| 4,137,910 A | * | 2/1979 | Murphy | 600/513 |
| 5,265,011 A | * | 11/1993 | O'Rourke | 600/485 |
| 5,836,884 A | | 11/1998 | Chio | |
| 5,865,758 A | | 2/1999 | Louzianine | |
| 6,485,431 B1 | | 11/2002 | Campbell | |
| 2009/0030328 A1 | * | 1/2009 | Harpas et al. | 600/485 |

FOREIGN PATENT DOCUMENTS

| | | |
|---|---|---|
| EP | 1103217 A2 | 5/2001 |
| WO | 2005/084536 A1 | 9/2005 |

OTHER PUBLICATIONS

The timing of the reflected wave in the ascending aortic pressure predicts restenosis after coronary stent placement by Hiroyasu et al., Hypertension Research, vol. 27, No. 8, pp. 535-540, 2004.*
"Preferential Stiffening of Central Over Peripheral Arteries in Type 2 Diabetes" by Kimoto et al., Diabetes, vol. 52, 2003, pp. 448-452.*
"Determination of wave speed and wave separation in the arteries" by A.W. Khir et al., Journal of Biomechanics, vol. 34 2001, pp. 1145-1155.*

(Continued)

*Primary Examiner* — Patricia Mallari
*Assistant Examiner* — Vasuda Ramachandran
(74) *Attorney, Agent, or Firm* — Andrus Intellectual Property Law, LLP

(57) ABSTRACT

A method for determination of cardiac output from a recording of an arterial pressure waveform (10). The method comprises the steps of measuring the patient's peripheral arterial pressure relative to time in order to estimate a central pressure waveform (CPW) and calculating the patient's cardiac output from the CPW using the Water Hammer formula (as defined herein).

21 Claims, 2 Drawing Sheets

(56) References Cited

OTHER PUBLICATIONS

"Physical basis of pressure transfer from periphery to aorta: a model-based study" by Nikos Stergiopulos et al., American Journal of Physiology—Heart and Circulatory Physiology, vol. 274, pp. 1386-1392, 1998.*

International Search Report dated Sep. 25, 2007.

Khir, A.W. et al., "Arterial Waves in Humans During Peripheral Vascular Surgery", Clinical Science (2001), vol. 101, pp. 749-757.

Stergiopulos, N. et al., "Physical Basis of Pressure Transfer from Periphery to Aorta: a Model-Based Study", Am. J. Physiol. Heart Circ. Physiol. (1998), vol. 274; 1386-1392.

Avolio, A.P. et al., "Effects of Aging on Changing Arterial Compliance and Left Ventricular Load in a Northern Chinese Urban Community", Circulation (1983), vol. 68, pp. 50-58.

* cited by examiner

METHOD FOR DETERMINATION OF CARDIAC OUTPUT

CROSS-REFERENCE TO RELATED APPLICATIONS

This application is the U.S. national stage application of International Application PCT/AU2007/001090 filed Aug. 3, 2007, which international application was published on Mar. 6, 2008, as International Publication WO 2008/025053 in the English language. The International Application claims priority to Australian Provisional Application No. 2006904754, filed Aug. 31, 2006.

FIELD OF THE INVENTION

The present invention relates to a method for determination of cardiac output from a recording of an arterial pressure waveform.

BACKGROUND OF THE INVENTION

A clinical and scientific goal for many years has been to determine cardiac output (i.e. blood flow ejected from the heart) from an arterial pressure measurement. The arterial pressure and flow pulse waveform is created by this ejection, but on account of: differences in arterial properties with age; differences in the pattern of flow ejection to the heart with age; weakening of the left ventricular muscle; and change in the heart rate under resting conditions, this goal has not yet been obtained with precision. An accurate determination of cardiac output is useful for diagnosis of cardiovascular diseases and clinically evaluating cardiac function. Cardiac output is also used as a guide in monitoring the therapeutic effects of a treatment in clinical situations.

Many methods are known for estimating cardiac output, either invasively or non-invasively, as there is no way to directly measure cardiac output. The Swan-Ganz thermodilution and the Dilution methods using the Stewart-Hamilton equation are the most used and accurate in measuring cardiac output. However, a disadvantage of these methods is that they are invasive procedures, which limits their application.

A non-invasive method uses Fick's principle to correlate the consumption of Oxygen, measured by a spirometer, with cardiac output. However, a disadvantage of this method is that it is time consuming due to the difficulty of collecting and analysing the gas concentrations.

Another non-invasive method requires echocardiography using an ultrasound Doppler probe to measure flow waves with echocardiographic measurements of aortic cross sectional area to calculate cardiac output (GE Healthcare, USA; Philips, The Netherlands). However, disadvantages of this method include that: its accuracy is dependant on the skill and accuracy of the probe location; and it is dependant on other measurements beside the flow waveform.

The PiCCO (PULSION Medical Systems AG, Munich, Germany) and PulseCO (LiDCO Ltd, London, England) technologies analyse arterial pressure waveforms to estimate cardiac output. These methods can estimate continuous cardiac output. However, a disadvantage of these methods is that they require an invasive calibration using either transpulmonary thermodilution or lithium dilution techniques, which diminishes their suitability for use as clinical devices.

The FloTrac method (Edward Lifesciences, USA) does not require independent calibration and estimates cardiac output and stroke volume from an arterial pressure waveform only. Disadvantages of this method include that: the calculation is based on a statistical model that correlates beat to beat stroke volume with beat to beat pulse pressure, age, gender and body surface area and the accuracy of the method is dependant on the accuracy of measurements used in calculating the model and on the size and representativeness of the population used to establish the model; and this technology requires an invasive arterial pressure waveform, which limits its suitability for a clinical application.

Another non-invasive method for estimating cardiac output is the thoracic bio-impedance method, which measures changing impedance in the chest as the heart beat changes fluid volumes and from this estimates cardiac output. Examples of such products are Bio-Z (Cardiodynamics Inc, USA) and PhysioFlow (Manatec Biomedical, France). Disadvantages of this method include that it: is expensive, both in terms of capital equipment cost and the consumables used per test; takes a relatively long time to set up sensors and stabilise readings; and still requires more than one signal (ECG, SpO2, and phonocardiogram) to calculate cardiac output.

Another non-invasive method for estimating cardiac output is the use of Doppler ultrasound to measure aortic blood flow (e.g. the USCOM device, USCOM Limited, Australia). Disadvantages of this method include that it: requires a carefully located and maintained Doppler sensor "looking" through the suprastemal notch at blood flow in the ascending aorta; requires operator skill not commonly available in a primary care doctor's office setting; and is expensive.

International PCT Patent Application No. PCT/AU2005/000311 (published as WO 2005/084536) discloses a method and apparatus for determining cardiac output from a peripheral pressure waveform. However, the disclosed method, which is broken down into 8 basic steps, suffers from the following disadvantages.

In relation to step 3, the disclosed method relies on a linear equation to calculate aortic Pulse Wave Velocity (PWV) from Age. The PWV equation was not mentioned in the reference cited, but estimated indirectly. Therefore, this equation is of questionable accuracy. Furthermore, in regard to the PWV measurement used to calculate the equation, there are only two types of aortic PWV measurements: invasive; and non invasive. If PWV was measured invasively, then (due to the necessary invasive procedures) the equation had to be derived from people suffering from cardiovascular disease. The disadvantage of such an invasive approach is the equation is thus not representative of a healthy population. If PWV was measured non-invasively, then the equation had to use a surrogate measurement of aortic PWV, which means that the equation does not relate aortic PWV with age but other PWV measurements, which will increase the error in the ensuing calculation of peak flow that uses aortic PWV. Also, the PWV equation assumes that PWV is linear with age. However, this is also questionable as other papers show a nonlinear relationship between age and aortic PWV.

In relation to step 4, the equation used to adjust aortic PWV to mean pressure was not mentioned in the associated reference, which casts doubt on the equation's accuracy.

In relation to steps 6-8, the equations used to adjust the flow for age and heart rate are not referenced. The accuracy of these equations is thus questionable. Further, the reason for all these adjustments is the unavailability of flow wave (either estimated or measured). This will make all of the flow adjustment equations less accurate.

By way of further background, the disclosure of the Applicant's International PCT Patent Application no. PCT/AU2006/001789, now U.S. Pat. No. 8,273,030, entitled: A method of estimating Pulse Wave Velocity (hereafter referred to as "the PWV application") is incorporated herein by cross reference. The PWV application discloses a method of calculating aortic PWV from central pressure waveform (CPW) by decomposing CPW into forward and reflected waveforms (referred to herein as the "AVI calculation").

OBJECT OF THE INVENTION

It is an object of the present invention to substantially overcome, or at least ameliorate, one or more of the above disadvantages.

SUMMARY OF THE INVENTION

Accordingly, in a first aspect, the present invention provides a method for determination of cardiac output from a recording of an arterial pressure waveform, the method comprising the following steps:
 a) measuring the patient's peripheral arterial pressure relative to time in order to estimate a central pressure waveform (CPW); and
 b) calculating the patient's cardiac output from the CPW using the Water Hammer formula (as defined herein).

In a second aspect, the present invention provides a method for determination of cardiac output from a recording of an arterial pressure waveform, the method comprising the following steps:
 a) measuring the patient's peripheral arterial pressure relative to time in order to estimate a central pressure waveform (CPW);
 b) estimating, from the CPW, forward Pressure pulse height ($P_f$), flow waveform and Pulse Wave Velocity (PWV) in the ascending aorta;
 c) calculating a peak velocity fluctuation V in the ascending aorta using the following Water Hammer formula: $V = P_f / (\rho * PWV)$, where $\rho$ is the density of blood;
 d) calibrating an aortic flow waveform from the estimated flow waveform using V; and
 e) calculating the patient's cardiac output from the calibrated aortic flow waveform.

In connection with the second aspect above it should be noted that, since the velocity starts at zero, then V is the peak velocity.

The method preferably also includes calculating Peak Flow Rate (PFR) by multiplying the velocity fluctuation V by the cross sectional area of the aorta, as follows:

$$PFR = V \times \pi \left(\frac{D}{2}\right)^2$$

where D is the aortic diameter.

The method preferably also includes calculating Mean Flow from the calibrated aortic flow waveform, more preferably deriving Mean Flow from an analysis of the CPW calibrated using the Water Hammer formula. In a preferred form, the method preferably includes respectively calculating and estimating aortic reflection time (ART), aortic PWV using the method disclosed in the PWV application and ejection duration (ED) from the CPW. The method preferably also includes using the method disclosed in the PWV application to create a flow waveform that, after calibrating such that the PFR is equal to the peak of the flow waveform, creates the calibrated flow waveform. The method preferably also includes calculating a Mean Flow by integrating the calibrated aortic flow waveform.

The method preferably also includes calculating Stroke Volume using the following formula:

Stroke Volume = Mean Flow × ED

The method preferably also includes calculating Cardiac Output using the following formula:

Cardiac Output = Stroke Volume × Heart Rate

The patient's aortic arterial distance is preferably estimated from: the patient's physical characteristics; a ratio of the carotid to femoral arterial distance; or measuring the superficial distance between sternal notch to the level of the umbilicus. The patient's carotid to femoral arterial distance is preferably estimated from the patient's height, weight and body mass index (BMI). Alternatively, a direct measurement of the distance between the carotid and femoral artery can be made, or the path length can be estimated from superficial body surface measurements. The ascending aortic pulse wave velocity (PWV) is preferably calculated by dividing the aortic arterial distance by the aortic pulse reflection time.

The patient's peripheral arterial pressure measurement is preferably taken at a single site. The patient's peripheral arterial pressure measurement can be taken non-invasively or invasively.

In a preferred (non-invasive) form, the patient's peripheral arterial pressure measurement is taken using the Applicant's SphygmoCor Px (Trade Mark) Pulse Wave Analysis system. The patient's radial artery pressure waveform is preferably measured, which is then used to derive the patient's CPW.

In an (invasive) embodiment, step 1 is performed by measuring a direct invasive radial artery recording of pressure and the central pressure waveform is calculated using the SphygmoCor system.

In another (invasive or non-invasive) embodiment, step 1 is performed on an average radial pulse from a continuous radial pressure waveform recording for every respiratory cycle, most preferably about 5-10 seconds, wherein each average pulse represents the radial pressure waveform in one respiratory cycle.

In yet another (invasive or non-invasive) embodiment, step 1 is performed on a radial pulse from a continuous radial pressure waveform recording on a beat to beat basis.

The method preferably includes determining the following parameters, most preferably with the Applicant's SphygmoCor Px (Trade Mark) Pulse Wave Analysis system and the method disclosed in the PWV application:
 i. The forward Pressure pulse height ($P_f$) in mmHg;
 ii. Aortic Pulse Reflection Time (ART) in msec;
 iii. Un-calibrated flow waveform;
 iv. Ejection Duration (ED) in msec;
 v. Heart Rate (HR) in beats/min; and
 vi. Carotid to Femoral distance (C-F Dist) in mm.

BRIEF DESCRIPTION OF THE DRAWINGS

Preferred embodiments and examples of the present invention will now be described, by way of examples only, with reference to the accompanying drawings, wherein.

DETAILED DESCRIPTION OF THE PREFERRED EMBODIMENTS AND EXAMPLES

Figure 1:
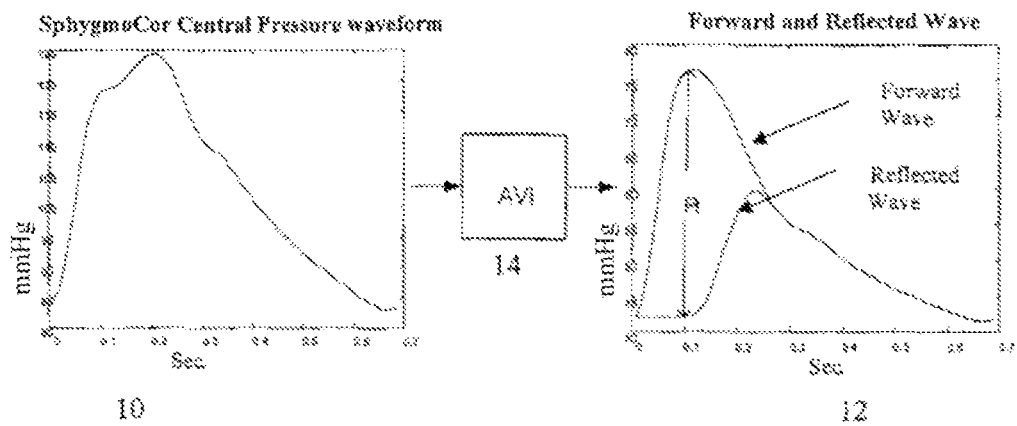
FIG. 1 is a flowchart showing a sample plot of a central pressure waveform 10 (CPW) versus time that is decomposed (i.e. the AVI calculation 14) into a plot of forward and reflected pressure waveforms 12 via the method disclosed in the PWV application.

FIG. 1 shows a plot 10 of an ascending aortic pressure waveform and a plot 12 of a deconstruction of the pressure wave into two components: the Forward Wave, which is related to left ventricular activities as a result of the heart's contraction; and the Reflected Wave, which is related to, and mainly reflects, arterial elastic properties. This deconstruction provides a better understanding of the interaction between cardiac and vascular activities and allows for waveform features to be directly related to either cardiac or vascular activity. A calculation of Aortic Pulse Reflection Time (ART) can be made from the plots 10 and 12 using the method disclosed in the PWV application, as will be described in more detail below.

An embodiment of the method for determining cardiac output from a non-invasive pressure measurement of a patient will now be described which allows determination of cardiac output. More particularly, the embodiment allows the forward and reflected waves shown in the plot 12 to be calculated non-invasively from parameters available from the Applicant's SphygmoCor (Trade Mark) system (hereafter "the SphygmoCor system") in pulse wave analysis mode utilising the method disclosed in the PWV application. The features from these waves relate to cardiac output.

The general steps in the embodiment of the method for determining cardiac output are as follows:

1. The aortic pressure transit time, both forward and reflected pressure waves (FPW and RPW) are calculated from an arterial, non-invasive central pressure waveform (CPW) measurement that is taken using the SphygmoCor system. To decompose the waveforms, an estimate of the flow wave is needed.
   The SphygmoCor system is then used, in accordance with the method disclosed in the PWV application, to determine the following parameters:
   i. The forward Pressure pulse height ($P_f$) in mmHg;
   ii. Aortic Pulse Reflection Time (ART) in msec;
   iii. Un-calibrated flow waveform;
   iv. Ejection Duration (ED) in msec;
   v. Heart Rate (HR) in beats/min; and
   vi. Carotid to Femoral distance (C-F Dist) in mm.
2. $P_f$ is then converted from mmHg to dynes/cm$^2$ using the following formula:

$P_f$(in dynes/cm$^2$)=$P_f$(in mmHg)×1.36 ×980

3. The aortic distance (Aor Dist) is then determined by measuring the superficial distance between the sternal notch to the level of the umbilicus.
4. The ascending aortic pulse wave velocity (PWV) is then calculated by the following formula:

$PWV$=(Aor Dist)/ART—where Aor Dist is in cm, and ART is in seconds

5. The following water-hammer formula (which relates pressure to velocity in the arteries ignoring pressure wave reflection) is then used to calculate the peak velocity at the aorta:

$P_f$=(ρ*V*PWV)→V=$P_f$/(ρ*PWV)     [Ref (1)]

Where: $P_f$ is the forward Pressure pulse height (in dynes/cm$^2$), V is the peak velocity fluctuation in aorta (in cm/sec) (It is noted that, since the velocity starts at zero, then V is the peak velocity), PWV is the Pulse Wave Velocity in to Ascending Aorta (in cm/sec) and ρ is the density of blood (=1.05g/ml).

6. The ascending aorta cross sectional diameter per square meter of body surface area is calculated using the following formula:

$D_{PSM}$=(0.0654×Age)+12.63     [Ref (2)]

Where $D_{PSM}$ is the aortic diameter in mm per square meter of body surface area, and Age is in years.

7. The body surface area (BSA) is estimated from height and weight using the following Du Bois and Du Bois equation $BSA$=Mass$^{0.425}$×Height$^{0.725}$×71.84     [Ref(3)]

Where BSA is the body surface area in cm$^2$, Mass is the weight in kg, and Height in cm.

8. Aortic cross sectional diameter is then calculated as follows:

$D$=BSA×$D_{PSM}$

[or D as measured directly by other techniques; eg echocardiography]

9. The Peak Flow Rate (PFR) is then calculated by multiplying the velocity fluctuation with the cross sectional area of the aorta as follows:

$$PFR = V \times \pi \left(\frac{D}{2}\right)^2$$

Figure 2:
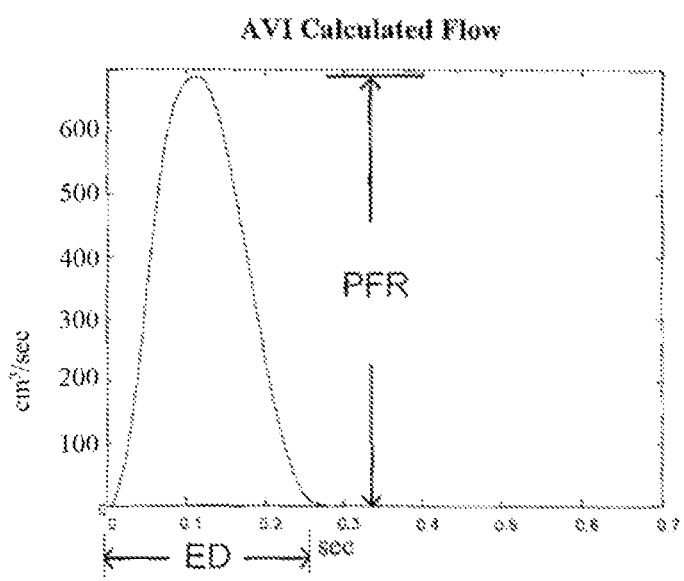
FIG. 2 is a plot of a sample calculated flow waveform.

10. The flow wave resulting from the method disclosed in the PWV application is then calibrated such that the PFR is equal to the peak of the flow waveform as shown in FIG. 2.
11. The average flow is then calculated by integrating the calibrated flow, using the following formula:

$$MeanFlow = \int_0^{ED} Flow(t)dt$$

12. The Stroke Volume is then calculated using the following formula:

Stroke Volume (in mL)=Mean Flow (in cm$^3$/sec)×$ED$ (in sec)

13. Finally, cardiac output can then be calculated using the following formula:

CO (mL/min)=Stroke Volume (mL/beat)×HR (beat/min)

If desired, other useful parameters can be calculated using the following formulas:

Impedance=Fourier transform (Pressure wave)/Fourier transform (Flow Wave)

Arterial compliance=Change in Volume/Change in Pressure

Peripheral resistance=mean (Pressure)/mean (flow)

The references referred to above are as follows:
1—Equation 9.1 in "Blood Flow in Arteries" McDonald D A, London 1960.
2—Lakatta E G. "Cardiovascular aging in health" *Clinics in Geriatric Medicine.* 16(3):419-44, 2000.

3—Dubois and Dubois (Arch.) Intern. Med 1916; 17:863.

Two examples of determining a patient's cardiac output using the embodiment of the method described above are set out below.

Figure 3:
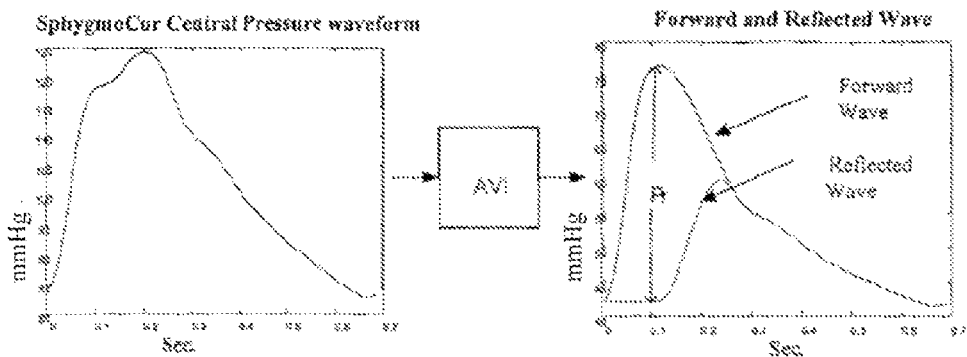
FIG. 3 is flowchart showing a plot of central pressure waveform (CPW) versus time that is decomposed into a plot of forward and reflected pressure waveforms via the method disclosed in the PWV application for a first example.
Figure 4:
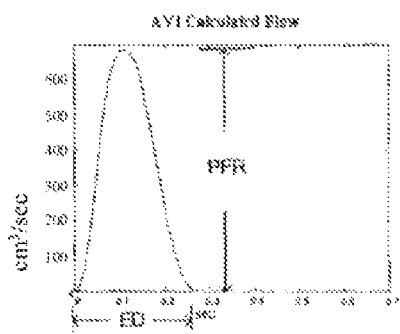
FIG. 4 is a plot of a calculated flow waveform for the first example.

FIRST EXAMPLE (see FIGS. 3 and 4 for plots)

Subject information: Male, 41 years, 178 cm Ht, 70 Kg Wt.
Data from the SphygmoCor system:
ED=315 ms
HR=67 bpm
Sampled Frequency=128 Hz;
Results from analysis of the data from the SphygmoCor system using the method disclosed in the PWV application:
P1_Height=Forward Pressure Pulse Height=$P_f$=22 mmHg
Aortic Pulse Reflection Time=129 ms
Entered Data:
Aortic Distance=311 mm
Calculations:

1. Convert P1_Height to dynes/cm²:

$$P1\_Height\ (in\ dynes/cm2) = P1\_Height\ (in\ mmHg) \times 1.36 \times 980$$

$$P1\_Height = 22 \times 1.36 \times 980 = 29322\ dynes/cm^2$$

2. Calculate Aortic Diameter in mm per square meter of body surface area ($D_{PSM}$):

$$D_{PSM} = (0.0654 \times Age) + 12.63$$

$$D_{PSM} = (0.0654 \times 41) + 12.63 = 15.311\ mm/m^2$$

3. Calculate Body Surface Area (BSA):

$$BSA = Mass^{0.426} \times Height^{0.725} \times 71.84$$

$$BSA = (70)^{0.426} \times (178)^{0.725} \times 71.84 = 18790\ cm^2 = 1.879\ m^2$$

4. Calculate Aortic diameter D in cm:

$$D = D_{PSA} \times BSA = 15.31 \times 1.879 = 28.771\ mm = 2.8771\ cm$$

5. Calculate Aortic Cross-sectional area in cm²:

$$Area = \pi\left(\frac{D}{2}\right)^2 = 6.501\ cm^2$$

6. Calculate Aortic Pulse Wave Velocity (Aortic PWV):

$$AorticPWV = \frac{AorticDistance}{AorticReflectionTime}$$

$$= \frac{311\ mm}{129\ ms}$$

$$= 2.4\ m/s$$

7. Calculate, using water-hammer formula, Peak flow in cm/sec:

$$PeakFlow = \frac{P_1 Height(dynes/cm^2)}{1.05 \times AorticPWV(cm/sec)}$$

$$= \frac{29322\ dynes/cm^2}{1.05 \times 241.2}$$

$$= 115.74\ cm/sec$$

8. Calculate Peak Flow Rate (PFR) in cm³/sec:

$$PFR = PeakFlow \times Area = 115.74 \times 6.501 = 752.43\ cm^3/sec$$

9. Calibrate the flow waveform resulting from the method disclosed in the PWV application such that the PFR is equal to the maximum of the flow waveform (see FIG. 4).

10. From the Waveform: calculate the mean Flow in cm³/sec:

$$MeanFlowRate = \frac{1}{N} \sum_{t=0}^{ED} flow(t)$$

$$= 348\ cm^3/sec$$

Where N=number of sampled flow points during ejection (sampling frequency=128Hz)

11. Calculate Stroke Volume (SV) in ml, using the following formula:

$$SV = MeanFlowRate(cm^3/sec) \times ED(sec) = 348 \times 0.315 = 109.72\ mL$$

12. Calculate Cardiac Output from SV as follows:

$$CardiacOutput = SV(mL/beat) \times HR(beat/min) = 109.72 \times 67 = 7351\ mL/min = 7.351\ L/min$$

Figure 5:
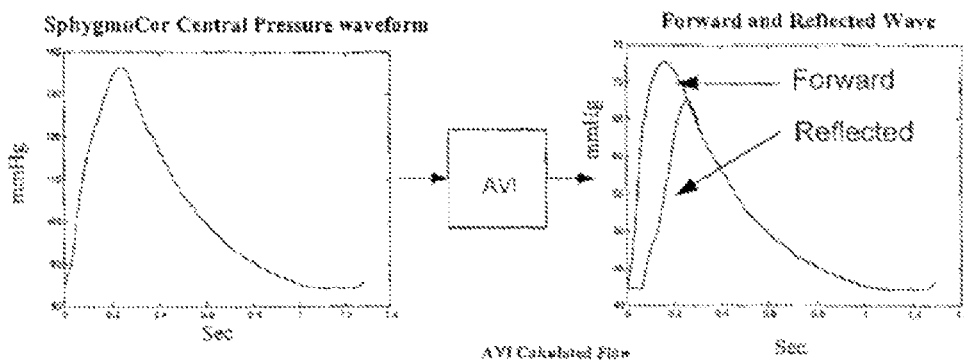
FIG. 5 is flowchart showing a plot of central pressure waveform (CPW) versus time that is decomposed into a plot of forward and reflected pressure waveforms via the method disclosed in the PWV application for a second example.
Figure 6:
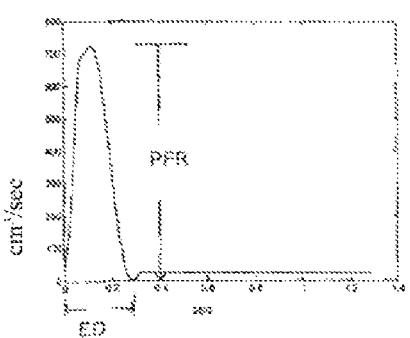
FIG. 6 is a plot of a calculated flow waveform for the second example.

SECOND EXAMPLE (see FIGS. 5 and 6 for plots)

Subject information: Male, 71 years, 179 cm Ht, 72 Kg Wt.
Data from the SphygmoCor system:
ED=327 ms
HR=47 bpm
Sampled Frequency=128 Hz;
Results from analysis of the data from the SphygmoCor system using the method disclosed in the PWV application:
P1_Height=Forward Pressure Pulse Height=$P_f$=30 mmHg
Aortic Pulse Reflection Time=102 ms
Entered Data:
Aortic Distance=459 mm
Calculation:

1. Convert P1_Height to dynes/cm²:

$$P1\_Height\ (in\ dynes/cm^2) = P1\_Height\ (in\ mmHg) \times 1.36 \times 980$$

$$P1\_Height = 30 \times 1.36 \times 980 = 39984\ dynes/cm^2$$

2. Calculate Aortic Diameter in mm per square meter of body surface area ($D_{PSM}$):

$$D_{PSM} = (0.0654 \times Age) + 12.63$$

$$D_{PSM} = (0.0654 \times 71) + 12.63 = 17.273\ mm/in^2$$

3. Calculate Body Surface Area (BSA):

$$BSA = Mass^{0.426} \times Height^{0.725} \times 71.84$$

$$BSA = (72)^{0.426} \times (179)^{0.725} \times 71.84 = 19095\ cm^2 = 1.9095\ m^2$$

4. Calculate Aortic diameter in cm D:

$$D = D_{PSA} \times BSA = 17.27 \times 1.9095 = 32.983\ mm = 3.298\ cm$$

5. Calculate Aortic Cross-sectional area in cm²:

$$Area = \pi\left(\frac{D}{2}\right)^2 = 8.544\ cm^2$$

6. Calculate Aortic Pulse Wave Velocity:

$$AorticPWV = \frac{AorticDistance}{AorticReflectionTime}$$

$$= \frac{459 \text{ mm}}{102 \text{ ms}}$$

$$= 4.5 \text{ m/s}$$

7. Calculate, using water-hammer formula, Peak flow in cm/sec:

$$PeakFlow = \frac{P_1 \text{Height(dynes/cm}^2)}{1.05 \times AorticPWV\text{(cm/sec)}}$$

$$= \frac{39984 \text{ dynes/cm}^2}{1.05 \times 450}$$

$$= 84.622 \text{ cm/sec}$$

8. Calculate Peak Flow Rate (PFR) in cm³/sec:

$PFR = \text{PeakFlow} \times \text{Area} = 84.62 \times 8.54 = 723.01 \text{ cm}^3/\text{sec}$ 9. Calibrate the flow waveform resulted from AVI calculation such that the PFR is equal to the maximum of the flow waveform (see FIG. 6).
10. From the Waveform: calculate the mean Flow in cm³/sec:

$$MeanFlowRate = \frac{1}{N} \sum_{t=0}^{ED} \text{flow}(t)$$

$$= 346 \text{ cm}^3/\text{sec}$$

Where
$N$=number of sampled flow points during ejection (sampling frequency=128 Hz)

11. Calculate Stroke Volume (SV) in mL, using the following formula:

$SV = \text{MeanFlowRate(cm}^3/\text{sec)} \times ED\text{(sec)} = 346 \times 0.327 = 113.19 \text{ mL}$ 12. Calculate Cardiac Output from SV as follows:

$\text{CardiacOuput} = SV\text{(mL/beat)} \times HR\text{(beat/min)} = 113.19 \times 47 = 5320 \text{ mL/min} = 5.32 \text{ L/min}$ The advantages of the embodiment of the method for determining cardiac output described above are as follows. Firstly, the embodiment relies on fewer assumptions and does not require an approximation of flow, which improves accuracy. Secondly, PWV can be calculated directly from the estimated aortic reflection time, which also improves accuracy. Thirdly, a calibrated flow waveform results from using this method, which provides added information on the cardiac function. Finally, other variables like Impedance, arterial compliance and resistance can subsequently be calculated, which will indicate the status of the cardiovascular system.

In a further embodiment, step 1 is performed by measuring a direct invasive radial artery recording of pressure and the central pressure waveform is calculated using the Sphygmo-Cor system. Steps 2 to 13 are as previously described.

In another embodiment, step 1 is performed on an average radial pulse from a continuous radial pressure waveform recording for every respiratory cycle (about 5-10 seconds) such that the each average pulse represent the radial pressure waveform in one respiratory cycle. Steps 2 to 13 are as previously described. In this embodiment, cardiac output is monitored continuously.

In yet another embodiment, step 1 is performed on a radial pulse from a continuous radial pressure waveform recording on a beat to beat basis. Steps 2 to 13 are as previously described. In this embodiment, cardiac output is monitored continuously and stroke volume is monitored on a beat to beat basis.

Although the invention has been described with reference to preferred embodiments, it will be appreciated by persons skilled in the art that the invention may be embodied in many other forms.

The invention claimed is:

1. A method for determination of cardiac output from a recording of an arterial pressure waveform, the method comprising the following steps:
   a) measuring the patient's peripheral arterial pressure relative to time and using a processor to estimate a central pressure waveform (CPW) from the patient's peripheral arterial pressure;
   b) estimating, using the processor, from the CPW, forward Pressure pulse height ($P_f$), flow waveform and Pulse Wave Velocity (PWV) in the ascending aorta;
   c) calculating a peak velocity fluctuation V in the ascending aorta using the following Water Hammer formula: $V = P_f / (\rho * PWV)$, where $\rho$ is the density of blood;
   d) calibrating an aortic flow waveform from the estimated flow waveform using V; and
   e) calculating the patient's cardiac output from the calibrated aortic flow waveform.

2. The method as claimed in claim 1, further including calculating Peak Flow Rate (PFR) by multiplying the velocity fluctuation V by the cross sectional area of the aorta, as follows:

$$PFR = V \times \pi \left(\frac{D}{2}\right)^2$$

where D is the aortic diameter.

3. The method as claimed in claim 1, further including calculating a Mean Flow from the calibrated aortic flow waveform.

4. The method as claimed in claim 3, wherein the Mean Flow is derived from an analysis of the CPW calibrated using the Water Hammer formula.

5. The method as claimed in claim 4, further including respectively calculating and estimating: aortic reflection time (ART); aortic PWV; and ejection duration (ED) from the CPW.

6. The method as claimed in claim 5, further including calculating the Mean Flow by integrating the calibrated aortic flow waveform.

7. The method as claimed in claim 6, further including calculating Stroke Volume using the following formula:

Stroke Volume=Mean Flow×ED.

8. The method s claimed in claim 7, further including calculating Cardiac Output using the following formula:

Cardiac Output=Stroke Volume×Heart Rate.

9. The method as claimed in claim 8, further including estimating the patient's aortic arterial distance from: the patents physical characteristics; a ratio of the carotid to femoral arterial distance; or measuring the superficial distance between sternal notch to the level of the umbilicus.

10. The method as claimed in claim 9, wherein the patient's carotid to femoral arterial distance is estimated form the patient's height, weight and body mass index (BMI).

11. The method as claimed in claim 9, wherein a direct measurement of the distance between the carotid and femoral artery is made.

12. The method as claimed in claim 9, wherein the patient's carotid to femoral arterial distance is estimated from superficial body surface measurements.

13. The method as claimed in claim 9, wherein the ascending aortic pulse wave velocity (PWV) is calculated by dividing the aortic arterial distance by the aortic pulse reflection time.

14. The method as claimed in claim 1, wherein the patient's peripheral arterial pressure measurement is taken at a single site.

15. The method as claimed in claim 14, wherein the patient's peripheral arterial pressure measurement is taken non-invasively.

16. The method as claimed in claim 14, wherein the patient's peripheral arterial pressure measurement is taken using a pulse wave analysis system.

17. The method as claimed in claim 14, wherein the patient's radial artery pressure waveform is measured, which is then used to derive the patient's CPW.

18. The method as claimed in claim 1, wherein step (a) is performed by measuring, a direct invasive radial artery recording of pressure and calculating the central pressure waveform.

19. The method as claimed in claim 1, wherein the step (a) is performed on an average radial pulse from a continuous radial pressure waveform recording for every respiratory cycle, wherein each average pulse represents the radial pressure waveform in one respiratory cycle.

20. The method as claimed in claim 1, wherein step (a) is performed on a radial pulse from a continuous radial pressure waveform recording on a beat to beat basis.

21. The method as claimed in claim 1, further including determining the following parameters:
   i. The forward Pressure pulse height ($P_f$) in mmHg.;
   ii. Aortic Pulse Reflection Time (ART) in milliseconds;
   iii. Un-calibrated flow waveform;
   iv. Ejection Duration (ED) in milliseconds;
   v. Heart Rate (HR) in beats/min; and
   vi. Carotid to Femoral distance (C-F Dist) in mm.

\* \* \* \* \*